(12) United States Patent
Shannon et al.

(10) Patent No.: US 6,521,785 B2
(45) Date of Patent: Feb. 18, 2003

(54) PESTICIDE FORMULATIONS CONTAINING ALKOXYLATED AMINE NEUTRALIZED AROMATICSULFONIC ACID SURFACTANTS

(75) Inventors: Tammy Tyler Shannon, Winfield, WV (US); Carolyn Estep Moore, Kernersville, NC (US); Victor Shui-Chiu Chow, Jamestown, NC (US)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 09/776,798

(22) Filed: Feb. 5, 2001

(65) Prior Publication Data

US 2002/0016264 A1 Feb. 7, 2002

Related U.S. Application Data

(63) Continuation of application No. PCT/EP99/05628, filed on Aug. 3, 1999.

(51) Int. Cl.⁷ ............................................. C07C 309/00
(52) U.S. Cl. ........................... 562/45; 562/84; 562/91; 562/114; 504/116.1; 516/201; 424/405; 424/84; 424/DIG. 9; 424/DIG. 10
(58) Field of Search ................. 562/84, 45, 91, 562/114; 504/116.1; 516/201; 424/405, 84, DIG. 9, DIG. 10

(56) References Cited

U.S. PATENT DOCUMENTS 2,686,201 A * 8/1954 Keenan ..................... 260/501
2,778,814 A * 1/1957 Behrens et al. ............. 260/98

FOREIGN PATENT DOCUMENTS

| EP | 0 074 329 A | 3/1983 | |
| FR | 2 297 843 A | 8/1976 | |
| WO | WO 95/17817 | * 7/1995 | .......... A01N/25/30 |

* cited by examiner

*Primary Examiner*—Paul F. Shaver
(74) *Attorney, Agent, or Firm*—William A. Teoli, Jr.; Thomas Hamilton

(57) ABSTRACT

The present invention relates to surfactants useful in life science and industrial formulations. More particularly, the invention relates to surfactants of alkoxylated amine neutralized by aromatic sulfonic acid and pesticide formulations containing the same.

20 Claims, No Drawings

PESTICIDE FORMULATIONS CONTAINING ALKOXYLATED AMINE NEUTRALIZED AROMATICSULFONIC ACID SURFACTANTS

"This is a continuation of International Application No. PCT/EP99/05628, filed Mar. 8, 1999, the contents of which are incorporated herein by reference"

FIELD OF THE INVENTION

The present invention relates to surfactants useful in life science and industrial formulations. More particularly, the invention relates to surfactants of alkoxylated amine neutralized by aromatic sulfonic acid and pesticide formulations containing the same.

BACKGROUND OF THE INVENTION

Alkylphenol ethoxylates (APEs) are a class of common industrial surfactants which are widely used in pesticide formulations. However, formulations containing APEs do not always provide the most desirable combination of design specifications, e.g. product efficacy, working parameters and cost. Traditional non-APE surfactant systems have not been readily adaptable substitutes for APE surfactants. For example, depending on the formulation requirements, calcium dodecylbenzesulfonate used in conjunction with fatty acid ethoxylates has proven to be an unacceptable APE substitute because of poor performance within one or more design parameters such as emulsion stability, acute toxicity, temporal and thermal stability, chemical and physical stability; solution, suspension or dilution dynamics, and viscosity and suspension stabilization. Phosphate esters, which are non-APE surfactants found in many types of formulations, suffer from long term stability problems due to undesirable transesterification and saponification reactions involving the mono-ester, di-ester, and free acid components of the surfactant mixture. The inability of industry to adapt existing technology to improve upon characteristics of surfactant systems containing APEs has prompted the development of entirely new line non-APE surfactant substitutes. The additional challenge faced by the scientific community has been to develop new non-APE substitutes which can be easily made from readily available and cost effective raw materials. Accordingly, there continues to be a need for other non-APE surfactant substitutes.

SUMMARY OF THE INVENTION

It has now been found that alkoxylated amine neutralized aromatic sulfonic acids are suitable as non-APE surfactant substitutes. The surfactants of the instant invention may be in the form of a surfactant salt compound, or composition containing one or more the surfactant compounds or salts. In one embodiment of the invention, the compositions containing the instant non-APE surfactants do not contain or are substantially free of alkylphenol ethoxylates (APEs). The surfactants of the instant invention are obtained from combining the appropriate aromatic sulfonic acid with the appropriate alkoxylated amine.

DETAILED DESCRIPTION OF THE INVENTION

One aspect of the invention is the salt compound of formula (I):

$$[(H\text{---}B)^+]_n A^{n-} \quad (I)$$

wherein $A^{n-}$ is the conjugate base of the acid H—A, wherein H—A is an aromatic sulfonic acid; and $(H\text{---}B)^+$ is the conjugate acid of the base B, wherein B is an alkoxylated amine, and n is the number of sulfonate anion groups or sulfonic acid groups on the conjugate base or acid respectively and with the proviso that HA and $A^{n-}$ may not contain a phenolic moiety. A "phenolic moiety" is defined as any phenyl ring containing at least one —OH group or any group developed by replacing the hydrogen of the —OH group with another organic or metal radical. The invention disclosed herein also includes a surfactant composition comprising a salt compound of formula (I). The invention also includes a pesticide formulation comprising at least one pesticide and a salt compound of formula (I).

A preferred aspect of the invention is the salt compound having the formula $[(H\text{---}B)^+]_n A^{n-}$ wherein $A^{n-}$ is the anion of the formula:

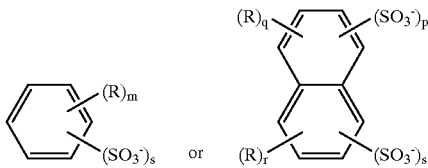

wherein each R is independently selected from the group consisting of $C_1$–$C_{24}$ alkyl, and $C_7$–$C_{24}$ alkylaryl, m is a number from 0 to 5, n is a number from 1 to 3, p is a number from 0 to 3, q is a number from 0 to 3, and r is a number from 0 to 4, s is a number from 1 to 3, and $(H\text{---}B)^+$ is the cation of the formula:

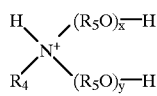

wherein $R_4$ is selected from the group consisting of hydrogen, $C_1$–$C_{24}$ alkyl and $C_2$–$C_{24}$ alkenyl—$CH_2$—, each $R_5$ independently is straight or branched chain $C_2$–$C_4$ alkylene, and x is a number from 1 to 50 and y is a number from 0 to 50, preferably x+y is number from 2 to 50 inclusive. A more preferred embodiment of the salt compound of formula $(H\text{---}B)^+ A^-$ wherein $A^-$ is the anion of the formula:

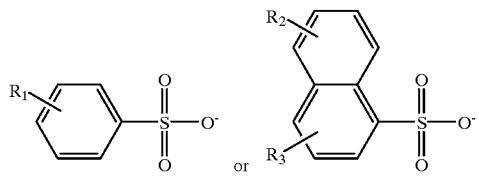

wherein $R_1$, $R_2$, and $R_3$ are independently selected from the group consisting of hydrogen and $C_1$–$C_{24}$ alkyl and $(H\text{---}B)^+$ is the cation of the formula:

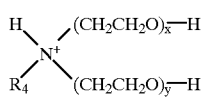

wherein $R_4$ is defined above (preferably n-octadecyl, n-hexadecyl and cis-9-octadecenyl); and x+y is a number from about 7 to 9 (preferably 8). Another more preferred embodiment of the invention is the salt compound wherein $A^-$ is an anion having the formula:

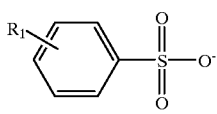

wherein $R_1$ is n-docecyl group.

The invention also is the compound or salt produced from the process of neutralizing an aromatic sulfonic acid of formula HA with an alkoxylated amine of formula B. The ammoniumsulfonate salt compounds or the product from the process of combining an aromatic sulfonic acid with an alkoxylated amine (to the extent there is a difference) are both features of the instantly disclosed invention. The scope of the invention disclosed herein should not be construed to be limited by any particular chemical theory relating to the complexation, equilibration, reaction or acid-base chemistry of the components used to make the surfactants or other ingredients used to make other ultimately useful formulations (e.g. pesticide formulations). In this regard, another aspect of the invention is the surfactant composition comprising one or more aromatic sulfonic acids and one or more alkoxylated amines wherein the constituent components may or may not have interacted chemically so as to result in a change in form of the components. The invention encompasses the static composition of the appropriate components admixed together as well as the chemically integrated surfactant composition comprising at least one aromatic sulfonic acid and at least one alkoxylated amine. "Static composition" denotes the composition composed of components wherein the components have not substantially changed by virtue of their combination with other composition components. "Chemically integrated composition" means a composition that results from the natural equilibration, complexation, dissociation or other chemical transformation if any that may occur after combination of the components and prior to ultimate use of the surfactant in a pesticide formulation. Therefore, the "chemically integrated composition" of the instant invention by definition encompasses the situation where there is a "static composition" as well as any resultant composition occurring at any point in time between initial creation and ultimate use in the field of products containing the surfactant. In other words, the disclosed invention is not limited to a static composition of chemically unaltered constituent components.

Another aspect of the invention is the surfactant composition produced as a whole from the combination of the aromatic sulfonic acid and the alkoxylated amine base to the extent it is composed of products other than ammoniumsulfonate salt compounds. Such a composition may contain chemically unaltered starting materials as well as other reaction products or by-products from reaction, equilibration, dissociation or complexation of the components in the composition.

The invention also includes the process for obtaining a surfactant which is useful as an APE substitute. In addition to the surfactant product or the product-by-process, the process of obtaining or making any of the surfactants herein disclosed is disclosed as part of the invention. The invention also includes the method of using the surfactant salt compounds of formula (I) and compositions thereof as APE substitutes.

The alkoxylated amines and the aromatic sulfonic acids used to make the surfactants of the invention are preferably those compounds that are readily available and inexpensive. However, cost of materials is only one factor in selecting the alkoxylated amines and the aromatic acids used as starting materials. After performing a routine cost-benefit analysis and in view of other design parameters it may become apparent that more expensive and less readily available starting materials may be preferred.

The aromatic sulfonic acids used in the instant invention may have one or more sulfonic acid groups and one or more groups attached to the aromatic moiety therein. The aromatic sulfonic acids may generally be defined by formulae II or III:

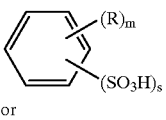

(II)

or

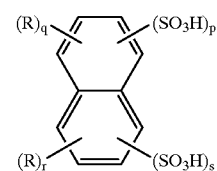

(III)

wherein each R, m, n, p, q, r and s are defined as above.

The preferred starting materials for making the surfactants of the instant invention are the compounds defined by formula IIa or IIIa:

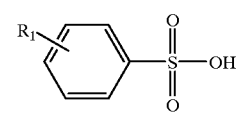

(IIa)

or

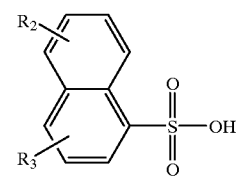

(IIIa)

wherein $R_1$, $R_2$, and $R_3$ are defined as above.

The preferred alkoxylated amines useful for making the surfactants of the instant invention are one or more of the compounds defined by formula IV:

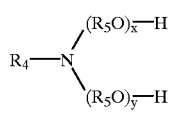

(IV)

wherein $R_4$, x and y are defined as above. A preferred feature of the invention is where the alkoxylated amines are one or more of the ethoxylated amines of formula V:

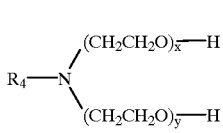

(V)

wherein $R_4$, x and y are defined as above. Additional preferred aspects of the invention are where $R_4$ is selected from the group consisting of n-octadecyl, n-hexadecyl and cis-9-octadecenyl, and x+y is a number from 5–10. Another preferred aspect of the invention is where the average x+y is a number from about 7 to 9 (more preferably 8).

Another aspect of the invention is the composition comprising the formulation of the surfactants disclosed above in formulations that contain one or more other active ingredients. A preferred embodiment of the invention is a pesticide formulation which contains the presently disclosed non-APE containing surfactants. However, the invention is not limited to pesticide formulations. Other useful formulations that may contain the instantly disclosed non-APE containing surfactants include shampoo formulations, detergent formulations generally and soap formulations used in the mining industry. The surfactants presently disclosed are considered to have general applicability as APE substitutes, and therefore would be expected to be useful in many other known formulations. The invention encompasses any formulation obtained by otherwise substituting the instantly disclosed surfactants for APEs as well as other surfactants. The instantly disclosed invention also encompasses any formulation obtained by supplementing compositions containing APEs with the instantly claimed surfactants. Generally, any formulation that conventionally makes use of surfactant additives would be subject to modification by substitution or supplementation with one or more of the surfactants of the instant invention. Although the compounds and compositions are referred to as "surfactants" in the instant application, it is expected that they will also have other nonsurfactant properties that may be useful independently of any inherent surfactant properties. Depending on the application of the instant invention, it may result in increased bioefficacy and/or reduced toxicity and irritation.

Another aspect of the invention is the composition comprising the formulation of the surfactants disclosed above in formulations that contain one or more herbicides and one or more safeners (antidote). When applying herbicides, the cultivated plants may also suffer severe damage owing to factors that include the concentration of the herbicide and the mode of application, the cultivated plant itself, the nature of the soil, and the climatic conditions such as exposure. A preferred embodiment of the invention is for example the formulation of the of s-metolachlor and benoxacor, or s-metolachlor, atrazine and benoxacor each in combination with the surfactants of the instant invention.

The surfactants are prepared by mixing the aromatic sulfonic acid of formula II or III with the alkoxylated amine of formula IV while controlling pH. The desired pH is maintained by precisely regulating the ratio of the acid and base components in the composition. For example, the appropriate acid-base ratio and desired pH can be achieved according to the following procedure: 1) A known weight of the aromatic sulfonic acid is dissolved in a 50/50 solution of isopropanol and water. 2) A tared amount of alkoxylated amine is slowly added to the aromatic sulfonic acid with constant stirring using a magnetic stirrer while pH is monitored by use of a pH meter fitted with a silver chloride electrode. 3) When the desired pH is attained, the amount of required alkoxylated amine is measured. 4) The ratio of aromatic sulfonic acid:alkoxylated amine (acid:base) is determined and the surfactant is prepared by mixing the appropriate amounts of the two components with stirring. For many of the pesticide formulations described herein the preferred acid:base ratio is approximately 35:65 (weight ratio). The acidity or basicity of the constituent components may vary depending on the supplier of the materials or the particular batch, therefore the pH is the controlling factor in preparing the compounds, compositions and formulations of the instant invention. The $pK_a$ and $pK_b$ for the aromatic sulfonic acid and the alkoxylated amine respectively may be varied to some extent by manipulating the type and degree of substitution for the compounds defined by formula II, III and IV. Therefore, the selection of the particular acid or base used will also effect the acid:base ratio used to make the surfactants as well as the desired pH. A preferred pH range for the surfactant is a pH from approximately 3–7, a more preferred pH range is from approximately 4 to 6, and an ultimately preferred pH range is from approximately 5–6. It is less desirable to adjust pH after the sulfonic acid and amine base components are mixed by the further addition of other acids or bases typically used to raise or lower pH because even minor amounts of additional salts can make a large difference in the observed properties of the product surfactant. It is also less desirable to have additional process steps or to have the added cost associated with purchasing, handling, storage and disposal of additional chemicals.

The emulsion stability of dodecylbenzenesulfonic acid neutralized with and ethoxylated tallow amine is typically greatest when the "average number of ethylene oxide units" (EO) on the tallow amine is 8 (i.e. 8 EO). "Average" is defined as the arithmetic mean of a set of real numbers (in this case the number of ethylene oxide units in the ethoxylated amines used to make the surfactant). A preferred feature of the invention is where there is a continuous and symmetrical bell curve population distribution around 8 EO. It is also desirable that there be low dispersion preferably within one standard deviation ($\sigma$) of the mean (average EO). A decrease in emulsification ability is observed when either 7 EO or 9 EO tallow amine was used to make the surfactant.

Some commercial suppliers and product names for the ethoxylated amines (i.e. amine ethoxylates) are:

| amine ethoxylate | Supplier* | Product Name | Average Number of EO |
|---|---|---|---|
| Tallow amines | Witco | Witcamine TAM-X0 (X = average number of OE) | 2, 4, 4.5, 5, 6, 7, 8, 9, 10 and 15 |
| Coco amines | Witco | Varonic K-2XX (XX = average number of EO) | 02, 05, 10 and 15 |
|  | Stephan | Toximul TA-X (X = average number of EO) | 2, 4, 4.5, 5, 6, 7, 8, 9, 10 and 15 |
| Oleyl amine | Witco | Varonic Q-202 | 2 |

*Addresses: Witco Corporation, 5777 Frantz Road, P.O. Box 646, Dublin, Ohio 43017. Stephan Company, Northfield, Illinois 60093.

One preferred aspect of the invention includes the combination of the surfactant compositions herein with a liquid pesticide compositions so as to obtain an emulsifiable concentrate formulation which can be directly mixed with water or other aqueous solution to give an aqueous pesticide formulation without special mixing procedures.

By "alkylaryl" is meant an aryl group substituted by one or more alkyl groups, wherein the "aryl" may be either a non-heteroaromatic ring system or heteroaromatic ring system.

The following examples illustrate further some of the aspects of the invention but are not intended to limit the its scope. Where not otherwise specified throughout this specification and claims, temperatures are given in degrees centigrade.

EXAMPLE 1

An oil-based suspension concentrate containing solid glyphosate as active ingredient was prepared according to the following formulation:

36.8% by weight solid glyphosate,
15.0% by weight linear dodecylbenzenesulfonic acid neutralized with tallow amine (8 EO),
0.1% by weight dimethyl polysiloxane as an antifoam agent
1.0% by weight fumed silicate as thickener, and a petroleum hydrocarbon solvent to make up 100%.

Other glyphosate salts may also be used in the invention, such as glyphosate-isopropylammonium, glyphosate-sesquisodium, or glyphosate-trimesium.

EXAMPLE 2

An aqueous suspension concentrate containing solid atrazine as active ingredient was prepared according to the following formulation:

43.5% by weight atrazine, 2.0% by weight linear dodecylbenzenesulfonic acid neutralized with tallow amine (8 EO), 1.15% by weight polyoxypropylene polyoxyethylene block copolymer, 0.10% by weight silicone antifoam, 0.15% by weight xanthan gum as thickener, 0.10% by weight preservative formaldehyde, and water to make up 100%.

A pregel is prepared by mixing thickener and water under high shear conditions. A slurry is prepared using the atrazine, the linear dodecylbenzenesulfonic acid neutralized with tallow amine (8 EO) and water. The slurry is ground to reduce particle size of atrazine. The pregel and remaining formulants are added and mixed until material is uniform.

EXAMPLE 3

An aqueous suspension concentrate containing solid atrazine as active ingredient was prepared in a manner analogous to that of Example 2 according to the following formulation:

43.5% by weight atrazine technical, 2.0% by weight branched dodecylbenzenesulfonic acid neutralized with coco amine (10 EO), 1.15% by weight polyoxypropylene polyoxyethylene block copolymer, 0.10% by weight silicone antifoam agent, 0.15% by weight xanthan gum as thickener, 0.10% by weight preservative formaldehyde, and water to make up 100%.

Viscosity of material=130 cps (Viscosity by Rotational (Brookfield) viscometer, ASTM Method D2196)

EXAMPLE 4

An aqueous suspension concentrate containing solid atrazine as active ingredient was prepared in a manner analogous to that of Example 2 according to the following formulation:

43.5% by weight atrazine, 2.0% by weight linear dodecylbenzenesulfonic acid neutralized with coco amine (15 EO), 1.15% by weight polyoxypropylene polyoxyethylene block copolymer, 0.10% by weight silicone antifoam agent, 0.15% by weight xanthan gum as thickener, 0.10% by weight preservative formaldehyde, and water to make up 100%.

Viscosity of material=125 cps (Viscosity by Rotational (Brookfield) viscometer, ASTM Method D2196)

EXAMPLE 5

An aqueous suspension concentrate containing solid atrazine as active ingredient was prepared in a manner analogous to that of Example 2 according to the following formulation:

43.5% by weight atrazine technical, 2.0% by weight linear dodecylbenzenesulfonic acid neutralized with tallow amine (9 EO), 1.15% by weight polyoxypropylene polyoxyethylene block copolymer, 0.10% by weight silicone antifoam agent, 0.15% by weight xanthan gum as thickener, 0.10% by weight preservative such as formaldehyde and water to make up 100%.

Viscosity of material=324 cps (Viscosity by Rotational (Brookfield) viscometer, ASTM Method D2196)

Additionally, one or more nonionic surfactant components may be used in the crop protection formulations. Nonionic surfactants are preferably polyglycol ether derivatives of aliphatic alcohols. The nonionic surfactants for example may be ethylenoxy/propylenoxy block polymers, castor oil ethoxylate and tristyarylphenol ethoxylate.

The crop protection compositions may be formulated in a form suitable for the intended application. Types of formulations include for example a flowable (FL) flowable concentrate for seed treatment (FS), wettable powder (WP), wettable dispersible granules (WDG), oil miscible flowable concentrate (OF), suspension concentrate (SC), emulsifiable concentrate (EC), liquid (L), water in oil emulsions (EW), granules (GR) water dispersible powder for slurry treatment (WS) and dry flowable (DF).

Some additional preferred embodiments of the instant invention are contained in Tables 1 and 2 below.

TABLE 1

Crop protection formulations containing surfactant, specified nonionic components and one or more active technical components.

|   | Aromatic sulfonic acid $R_1$ | Exthoxylated amine $R_4$ | (x + y) | Nonionic component | Active Technical $T_1$ | Active Technical $T_2$ | Active Technical $T_3$ |
|---|---|---|---|---|---|---|---|
| 1 | $C_{12}$ | $C_{16-18}$ | 8 | Butoxy EO/PO block polymer | metolachlor* | | |
| 2 | $C_{12}$ | $C_{12-14}$ | 3 | Butoxy EO/PO block polymer | metolachlor* | | |
| 3 | $C_{12}$ | $C_{16-18}$ | 4.5, 5, 6, 7, 8, or 9 | EO/PO block polymer | atrazine | | |
| 4 | $C_{12}$ | $C_{16-18}$ | 4.5, 5, 6, 7, 8, or 9 | nonylphenol EO/PO block polymer | atrazine | | |
| 5 | $C_{12,branched}$ | $C_{12-14}$ | 10 | EO/PO block polymer | atrazine | | |
| 6 | $C_{12,branched}$ | $C_{12-14}$ | 15 | EO/PO block polymer | atrazine | | |
| 7 | $C_{12}$ | $C_{16-18}$ | 4.5, 5, 6, 7, 8, or 9 | EO/PO block polymer | atrazine | | |

TABLE 1-continued

Crop protection formulations containing surfactant, specified nonionic components and one or more active technical components.

| | Aromatic sulfonic acid $R_1$ | Ethoxylated amine $R_4$ | $(x + y)$ | Nonionic component | Active Technical $T_1$ | Active Technical $T_2$ | Active Technical $T_3$ |
|---|---|---|---|---|---|---|---|
| 8 | $C_{12}$ | $C_{16-18}$ | 4.5, 5, 6, 7, 8, or 9 | Castor oil ethoxylate | atrazine | metolachlor* | |
| 9 | $C_{12}$ | $C_{16-18}$ | 4.5, 5, 6, 7, 8, or 9 | Butoxy EO/PO block polymer | atrazine | metolachlor* | |
| 10 | $C_{12}$ | $C_{16-18}$ | 8 | Castor oil ethoxylate | flumetralin | | |
| 11 | $C_{12}$ | $C_{16-18}$ | 8 | Castor oil ethoxylate | oxasulfuron | | |
| 12 | $C_{12}$ | $C_{16-18}$ | 8 | tristyrylphenol ethoxylate | propiconazole | | |
| 13 | $C_{12}$ | $C_{16-18}$ | 8 | Butoxy EO/PO block polymer | metribuzin | metolachlor* | |
| 14 | $C_{12}$ | $C_{12-14}$ | 3 | Butoxy EO/PO block polymer | metribuzin | metolachlor* | |
| 15 | $C_{12}$ | $C_{16-18}$ | 8 | Butoxy EO/PO block polymer | flumetsulam | metolachlor* | |
| 16 | $C_{12}$ | $C_{12-14}$ | 3 | Butoxy EO/PO block polymer | flumetsulam | metolachlor* | |
| 17 | $C_{12}$ | $C_{16-18}$ | 4.5, 5, 6, 7, 8, or 9 | Castor oil ethoxylate | flumetsulam | metolachlor* | atrazine |
| 18 | $C_{12}$ | $C_{16-18}$ | 4.5, 5, 6, 7, 8, or 9 | Butoxy EO/PO block polymer | flumetsulam | metolachlor* | atrazine |
| 19 | $C_{12}$ | $C_{16-18}$ | 8 | Butoxy EO/PO block polymer | mefenoxam | | |
| 20 | $C_{12}$ | $C_{12-14}$ | 3 | Butoxy EO/PO block polymer | mefenoxam | | |
| 21 | $C_{12}$ | $C_{16-18}$ | 8 | Butoxy EO/PO block polymer | metalaxyl | | |
| 22 | $C_{12}$ | $C_{12-14}$ | 3 | Butoxy EO/PO block polymer | metalaxyl | | |
| 23 | $C_{20-22}$ | $C_{16-18}$ | 4.5, 5, 6, 7, 8, or 9 | Butoxy EO/PO block polymer | diazinon | | |
| 24 | $C_{12}$ | $C_{16-18}$ | 4.5, 5, 6, 7, 8, or 9 | Butoxy EO/PO block polymer | diazinon | | |
| 25 | $C_{12}$ | $C_{16-18}$ | 4.5, 5, 6, 7, 8, or 9 | Butoxy EO/PO block polymer | dicamba | | |
| 26 | $C_{12}$ | $C_{16-18}$ | 4.5, 5, 6, 7, 8, or 9 | Castor oil ethoxylate | dicamba | | |
| 27 | $C_{12}$ | $C_{16-18}$ | 4.5, 5, 6, 7, 8, or 9 | Butoxy EO/PO block polymer | COMPOUND A | | |
| 28 | $C_{12}$ | $C_{16-18}$ | 4.5, 5, 6, 7, 8, or 9 | Castor oil ethoxylate | COMPOUND A | | |
| 29 | $C_{12}$ | $C_{16-18}$ | 4.5, 5, 6, 7, 8, or 9 | Butoxy EO/PO block polymer | glyphosate or salts | | |
| 30 | $C_{12}$ | $C_{16-18}$ | 8 | Butoxy EO/PO block polymer | glyphosate isopropylammonium | | |
| 31 | $C_{12}$ | $C_{16-18}$ | 8 | Butoxy EO/PO block polymer | glyphosate sesquisodium | | |
| 32 | $C_{12}$ | $C_{16-18}$ | 8 | Butoxy EO/PO block polymer | glyphosate trimesium | | |
| 33 | $C_{12}$ | $C_{16-18}$ | 4.5, 5, 6, 7, 8, or 9 | Butoxy EO/PO block polymer or castor oil ethoxylate | fluthiacet-methyl | | |
| 34 | $C_{12}$ | $C_{16-18}$ | 4.5, 5, 6, 7, 8, or 9 | Butoxy EO/PO block polymer or C13 branched alcohol | glyphosate or salts | fluthiacet-methyl | |
| 35 | $C_{12}$ | $C_{16-18}$ | 8 | Butoxy EO/PO block polymer | glyphosate isopropylammonium | fluthiacet-methyl | |
| 36 | $C_{12}$ | $C_{16-18}$ | 8 | Butoxy EO/PO block polymer | glyphosate sesquisodium | fluthiacet-methyl | |
| 37 | $C_{12}$ | $C_{16-18}$ | 8 | Butoxy EC/PO block polymer | glyphosate trimesium | fluthiacet-methyl | |
| 38 | $C_{12}$ | $C_{16-18}$ | 4.5, 5, 6, 7, 8, or 9 | Butoxy EO/PO block polymer | flumiclorac-pentyl | | |
| 39 | $C_{12}$ | $C_{16-18}$ | 4.5, 5, 6, 7, 8, or 9 | Butoxy EO/PO block polymer | glyphosate or salts | flumiclorac-pentyl | |

TABLE 1-continued

Crop protection formulations containing surfactant, specified nonionic components and one or more active technical components.

Aromatic sulfonic acid:

$$R_1\text{-}C_6H_4\text{-}SO_2\text{-}OH$$

Ethoxylated amine:

$$R_4\text{-}N((CH_2CH_2O)_x\text{-}H)((CH_2CH_2O)_y\text{-}H)$$

| # | $R_1$ | $R_4$ | (x + y) | Nonionic component | Active Technical $T_1$ | Active Technical $T_2$ | Active Technical $T_3$ |
|---|---|---|---|---|---|---|---|
| 40 | $C_{12}$ | $C_{16-18}$ | 8 | Butoxy EO/PO block polymer | glyphosate isopropylammonium | flumiclorac-pentyl | |
| 41 | $C_{12}$ | $C_{16-18}$ | 8 | Butoxy EO/PO block polymer | glyphosate sesquisodium | flumiclorac-pentyl | |
| 42 | $C_{12}$ | $C_{16-18}$ | 8 | Butoxy EO/PO block polymer | glyphosate trimesium | flumiclorac-pentyl | |
| 43 | $C_{12}$ | $C_{16-18}$ | 4.5, 5, 6, 7, 8, or 9 | Butoxy EO/PO block polymer | glufosinate or salts | | |
| 44 | $C_{12}$ | $C_{16-18}$ | 8 | Butoxy EO/PO block polymer | glufosinate | | |
| 45 | $C_{12}$ | $C_{16-18}$ | 8 | Butoxy EO/PO block polymer | glufosinate ammonium | | |
| 46 | $C_{12}$ | $C_{16-18}$ | 4.5, 5, 6, 7, 8, or 9 | Butoxy EO/PO block polymer | glufosinate or salts | fluthiacet-methyl | |
| 47 | $C_{12}$ | $C_{16-18}$ | 8 | Butoxy EO/PO block polymer | glufosinate | fluthiacet-methyl | |
| 48 | $C_{12}$ | $C_{16-18}$ | 8 | Butoxy EO/PO block polymer | glufosinate ammonium | fluthiacet-methyl | |
| 49 | $C_{12}$ | $C_{16-18}$ | 4.5, 5, 6, 7, 8, or 9 | Butoxy EO/PO block polymer | glufosinate or salts | flumiclorac-pentyl | |
| 50 | $C_{12}$ | $C_{16-18}$ | 8 | Butoxy EO/PO block polymer | glufosinate | flumiclorac-pentyl | |
| 51 | $C_{12}$ | $C_{16-18}$ | 8 | Butoxy EO/PO block polymer | glufosinate ammonium | flumiclorac-pentyl | |
| 52 | $C_{12}$ | $C_{16-18}$ | 8 | Butoxy EO/PO block polymer | glyphosate | atrazine | |
| 53 | $C_{12}$ | $C_{16-18}$ | 8 | Butoxy EO/PO block polymer | glyphosate | metolachlor* | atrazine |
| 54 | $C_{12}$ | $C_{16-18}$ | 8 | Butoxy EO/PO block polymer | glyphosate salt | atrazine | |
| 55 | $C_{12}$ | $C_{16-18}$ | 8 | Butoxy EO/PO block polymer | glyphosate salt | metolachlor* | atrazine |

*includes the racemic mixtures or s-metolachor
$R_1$ is linear unless otherwise indicated
x + y = EO (average # ethylene oxide units)

TABLE 2

Crop protection formulations:

Surfactant used: (defined in terms of starting materials)

$$R_1\text{-}C_6H_4\text{-}SO_2\text{-}OH \quad R_4\text{-}N((CH_2CH_2O)_x\text{-}H)((CH_2CH_2O)_y\text{-}H)$$

$R_1 = C_{8-22}$   $R_4 = C_{7-19}$
x + y = 2EO TO 15 EO

Active technical ingredients used and formulation type:

| ACTIVE TECHNICAL $T_1$ | ACTIVE TECHNICAL $T_2$ | ACTIVE TECHNICAL $T_3$ | FORMULATION TYPE |
|---|---|---|---|
| Atrazine | | | FL, WP, WDG, OF |
| Atrazine | Flumetsulam | | FL, WP, WDG, OF |
| Atrazine | Metolachlor | | SC, OF, WDG |
| Atrazine | Flumetsulam | Metolachlor | SC, OF, WDG |
| Ametryn | | | OF, EC, WP, L, WDG |
| Chlorothalonil | | | FL, WDG, WP |
| Chlorothalonil | Metalaxyl | | EC, WDG, WP, OF |
| Cyprodinil | | | EC, WP, OF, WDG |
| Cyromazine | | | WP, L |
| Diazinon | | | EW, W, EC, WDG |
| Dicamba | | | GR, L |
| Dicamba | Prosulfuron | | WDG |
| Difenoconazole | | | WP, EC, WS, FS |
| Difenoconazole | Metalaxyl | | WP, EC, WS, FS |
| Diofenolan | | | EC, WP |
| Fenoxycarb | | | WP, WDG, EC |
| Fenoxycarb | Pymetrozine | | WP, WDG, EC |
| Fludioxinil | | | L, FS, WDG, WP |
| Fludioxinil | Metalaxyl | | L, FS, WDG, WP |
| Fludioxinil | Propiconazole | | L, FS, WDG, WP |
| Flumetralin | | | EC, WDG, WP |
| Flumetralin | Oxasulfuron | | EC, WDG, WP |
| Flumetsulam | | | EC, WDG, WP, OF |
| Flumetsulam | Metolachlor | | EC, WDG, WP, OF |
| Fluometuron | | | L, DF, WP |
| Fluthiacet- | | | EC, WDG, WP, OF |

TABLE 2-continued

Crop protection formulations:

| | | |
|---|---|---|
| methyl | | |
| Fluthiacet-methyl | Glyphosate | EC, WDG, WP |
| Fluthiacet-methyl | Oxasulfuron | EC, WDG, WP |
| Isazofos | | EC, GR |
| Mancozeb | | SC, FL, WDG, WP |
| Mancozeb | Metalaxyl | SC, FL, WDG, WP |
| Mefenoxam | | EC, WP, GR, FL, L |
| Metalaxyl | | EC, GR, L, WP |
| Methidathion | | EC, WP |
| Metolachlor | | EC, DF, GR |
| Metolachlor | Metribuzin | WDG, OF, EC |
| Metolachlor | Simazine | WDG, OF, SC |
| s-Metolachlor | | EC, DF, GR |
| s-Metolachlor | Metribuzin | WDG, OF, EC |
| s-Metolachlor | Simazine | WDG, OF, SC |
| Metribuzin | | EC, DF, WDG, OF |
| Norflurazon | | DF, GR |
| Primisulfuron | | WDG, WP |
| Primisulfuron | Prosulfuron | WDG, WP |
| Profenofos | | EC |
| Prometon | | EC, FL, OF, WP |
| Prometryn | | WP, L, OF |
| Propiconazole | | EC, WP |
| Pymetrozine | | WDG, WP |
| Simazine | | WP, WDG, L, GR |
| Triforine | | WP, EC |
| Trinexapac-ethyl | | EC, WDG, |
| COMPOUND A | | WDG, OF, EC, SC |
| COMPOUND B | | WDG, WP |
| COMPOUND C | | WDG, WP, EC |
| COMPOUND D | | EC, WP, WDG |

EO = average number of ethylene oxide units

| Code | Description of formulation code |
|---|---|
| DF | dry flowable |
| EC | emulsifiable concentrate |
| EW | water in oil emulsions |
| FL | flowable |
| FS | flowable concentrate for seed treatment |
| GR | granules |
| L | liquid |
| OF | oil miscible flowable concentrate |
| SC | suspension concentrate |
| WDG | wettable dispersible granules |
| WP | wettable powder |
| WS | water dispersible powder for slurry treatment |

TABLE 3

Compound designations

| CGA Number | Structure |
|---|---|
| COMPOUND A | [structure: 2-chloro-thiazol-5-ylmethyl linked to N-methyl-N'-nitro-1,3,5-oxadiazinan-imine] |
| COMPOUND B | [structure: sodium salt of pyridine-2-sulfonyl-urea with 2,2,2-trifluoroethoxy group and 4,6-dimethoxypyrimidin-2-yl] |
| COMPOUND C | [structure: methyl (E)-2-{2-[(E)-1-(3-trifluoromethylphenyl)ethylideneaminooxymethyl]phenyl}-2-methoxyiminoacetate] |

TABLE 3-continued

Compound designations

| CGA Number | Structure |
|---|---|
| COMPOUND D | 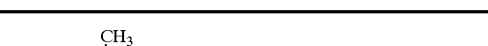 |

What is claimed is:

1. A salt compound of the formula $[(H-B)^{30}]_n A^{n-}$ wherein $A^{n-}$ is:

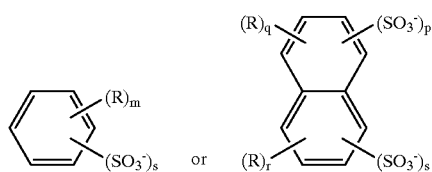

wherein each R is independently selected from the group consisting of $C_1-C_{24}$ alkyl and $C_7-C_{24}$ alkylaryl, m is a number from 0 to 5, n is a number from 1 to 3, p is a number from 0 to 3, q is a number from 0 to 3, and r is a number from 0 to 4, s is a number from 1 to 3, wherein $(H-B)^+$ is the cation of the formula:

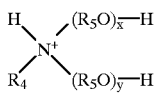

wherein $R_4$ is selected from the group consisting of $C_7-C_{24}$ alkyl and $C_2-C_{24}$ alkenyl—$CH_2$—, each $R_5$ independently is a straight chain or branched $C_2-C_4$ alkylene, x is a number from 1–50 and y is a number from 0 to 50, wherein the salt compound has a pH of 4 to 6.

2. A salt compound according to claim 1, having the formula $(H-B)^+A^-$ wherein $A^-$ is:

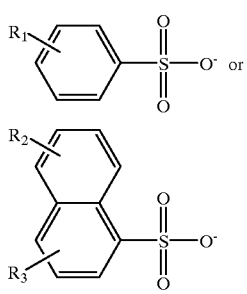

wherein $R_1$, $R_2$, and $R_3$ are independently selected from the group consisting of hydrogen and $C_1-C_{24}$ alkyl;

wherein $(H-B)^+$ is the cation of the formula:

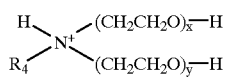

wherein x+y is a number from about 7 to 9, and $R_4$ is defined above.

3. A salt compound according to claim 2, wherein $A^-$ is an anion having the formula:

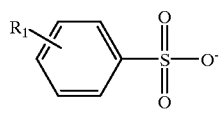

wherein $R_1$ is defined above.

4. A salt compound according to claim 3, wherein $R_1$ is a n-docecyl group.

5. A salt compound according to claim 4, wherein $R_4$ is selected from the group consisting of n-octadecyl, n-hexadecyl and cis-9-octadecenyl; and x+y is equal to 8.

6. A product obtained by the process of neutralizing at least one aromatic sulfonic acid of formulae II or III:

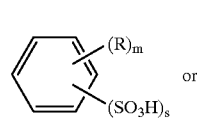

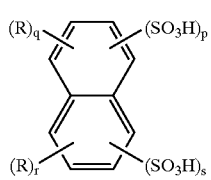

wherein each R is independently selected from the group consisting of hydrogen, $C_1-C_{24}$ alkyl and $C_7-C_{24}$ alkylaryl, m is a number from 0 to 5, n is a number from 1 to 3, p is a number from 0 to 3, q is a number from 0 to 3, and r is a number from 0 to 4, s is a number from 1 to 3, with at least one alkoxylated amine base of formula IV:

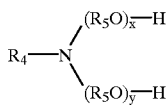
(IV)

wherein $R_4$ is selected from the group consisting of $C_7$–$C_{24}$ alkyl and $C_2$–$C_{24}$ alkenyl—$CH_2$—, each $R_5$ independently is a straight chain or branched $C_2$–$C_4$ alkylene, and the average x+y is a number from 2 to 50 inclusive, wherein the product has a pH of 4 to 6.

7. A product according to claim 6, where said at least one aromatic sulfonic acid is a compound defined by formula IIa or IIIa:

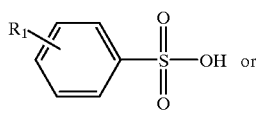
(IIa)

or

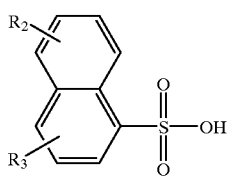
(IIIb)

wherein $R_1$, $R_2$, and $R_3$ are independently selected from the group consisting of hydrogen and $C_1$–$C_{24}$ alkyl; and said at least one ethoxylated amine base represented by the formula V:

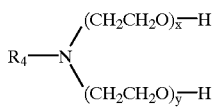
(V)

wherein $R_4$ is $C_7$–$C_{24}$ alkyl and the average x+y is a number from about 7 to 9.

8. A product according to claim 6, wherein the product surfactant has a pH of 5 to 6.

9. A surfactant composition comprising a salt of:
at least one aromatic sulfonic acid compound represented by the formulae II or III:

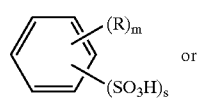
(II)

or

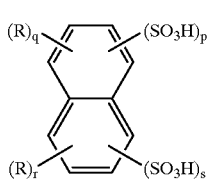
(III)

wherein each R is independently selected from the group consisting of $C_1$–$C_{24}$ alkyl and $C_7$–$C_{24}$ alkylaryl, m is a number from 0 to 5, n is a number from 1 to 3, p is a number from 0 to 3, q is a number from 0 to 3, and r is a number from 0 to 4, s is a number from 1 to 3, and at least one alkoxylated amine base represented by the formula IV:

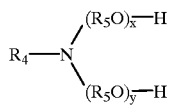
(IV)

wherein $R_4$ is selected from the group consisting of $C_7$–$C_{24}$ alkyl and $C_2$–$C_{24}$ alkenyl—$CH_2$—, each $R_5$ independently is a straight or branched chain $C_2$–$C_4$ alkylene, and the average x+y is a number from 2 to 50 inclusive, wherein the surfactant composition has a pH of 4 to 6.

10. A surfactant composition according to claim 9 wherein:
is at least one aromatic sulfonic acid compound represented by the formulae IIa or IIIa:

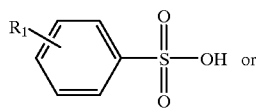
(IIa)

or

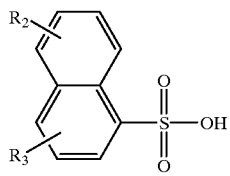
(IIIa)

wherein $R_1$, $R_2$, and $R_3$ are independently selected from the group consisting of hydrogen and $C_1$–$C_{24}$ alkyl; and
is at least one ethoxylated amine base represented by the formula V:

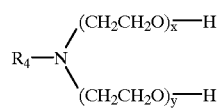
(V)

wherein $R_4$ is $C_7$–$C_{24}$ alkyl and x+y is a number from about 7 to 9.

11. A composition of claim 9, wherein the product surfactant has a pH of 5 to 6.

12. A chemically integrated surfactant composition comprising at least one aromatic sulfonic acid compound represented by formula II or III:

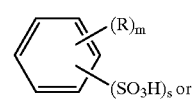
(II)

or with at least one ethoxylated amine wherein said aromatic sulfonic acid is represented by the formulae (II) or (III):

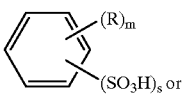

(II)

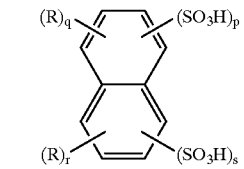

(III)

wherein each R is independently selected from the group consisting of $C_1$–$C_{24}$ alkyl and $C_7$–$C_{24}$ alkylaryl, m is a number from 0 to 5, n is a number from 1 to 3, p is a number from 0 to 3, q is a number from 0 to 3, and r is a number from 0 to 4, s is a number from 1 to 3, and the said alkoxylated amine is represented by the formula IV:

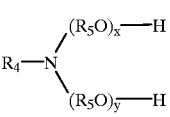

(IV)

wherein $R_4$ is selected from the group consisting of $C_7$–$C_{24}$ alkyl and $C_2$–$C_{24}$ alkenyl—$CH_2$—, each $R_5$ independently is a straight or branched chain $C_2$–$C_4$ alkylene, and the average x+y is a number from 2 to 50 inclusive, wherein the aromatic sulfonic acid neutralized with at least one ethoxylated amine has a pH of 4 to 6.

16. A pesticide formulation according to claim 15 wherein said aromatic sulfonic acid is represented by the formulae IIa or IIIa:

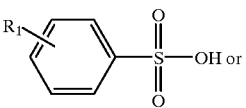

(II)

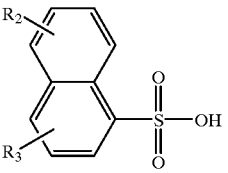

(III)

wherein $R_1$, $R_2$, and $R_3$ are independently selected from the group consisting of hydrogen and $C_1$–$C_{24}$ alkyl;

and the said ethoxylated amine is represented by the formula V:

---

-continued

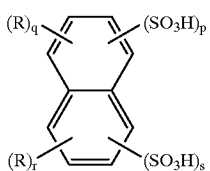

(III)

wherein each R is independently selected from the group consisting of $C_1$–$C_{24}$ alkyl and $C_7$–$C_{24}$ alkylaryl, m is a number from 0 to 5, n is a number from 1 to 3, p is a number from 0 to 3, q is a number from 0 to 3, and r is a number from 0 to 4, s is a number from 1 to 3, and at least one alkoxylated amine base represented by the formula IV:

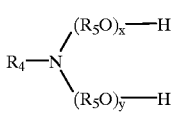

(IV)

wherein $R_4$ is selected from the group consisting of $C_7$–$C_{24}$ alkyl and $C_2$–$C_{24}$ alkenyl—$CH_2$—, each $R_5$ independently is a straight or branched chain $C_2$–$C_4$ alkylene, and the average x+y is a number from 2 to 50 inclusive, or the chemical interaction products thereof wherein the chemically integrated surfactant has a pH of 4 to 6.

13. A chemically integrated surfactant composition according to claim 12 where the aromatic sulfonic acid compound is defined by the formula IIa or IIIa:

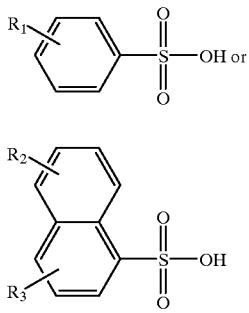

(II)

(III)

wherein $R_1$, $R_2$, and $R_3$ are independently selected from the group consisting of hydrogen and $C_1$–$C_{24}$ alkyl;
and at least one ethoxylated amine base represented by the formula V:

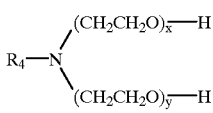

(V)

wherein $R_4$ is $C_7$–$C_{24}$ alkyl and x+y is a number from about 7 to 9.

14. A composition of claim 12, wherein the product surfactant has a pH of 5 to 6.

15. A pesticide formulation comprising at least one pesticide and at least one aromatic sulfonic acid neutralized

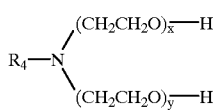 (V)

wherein $R_4$ is $C_7$–$C_{24}$ alkyl and x+y is a number from about 7 to 9.

17. A pesticide formulation of claim 15 wherein the at least one pesticide is selected from the group consisting of mefenoxam, s-metolachlor, flumetsulam, fluthiacet-methyl, atrazine and glyphosate.

18. A method of protecting crops comprising the step of applying to the locus of the crops in need of protection an agriculturally effective amount of the formulation of claim 15.

19. A method of protecting crops comprising the step of applying to the locus of the crops in need of protection an agriculturally effective amount of the formulation of claim 16.

20. A method of using the salt compounds of claim 1 as an APE substitute which comprises substituting an APE surfactant system in a formulation with the salt compounds having the formula $[(H-B)^+]_n A^{n-}$.

* * * * *